US005747032A

United States Patent [19]
Metcalf et al.

[11] Patent Number: 5,747,032
[45] Date of Patent: May 5, 1998

[54] MONOCLONAL ANTIBODY TO HUMAN GRANULOCYTE MACROPHAGE COLONY STIMULATING FACTOR

[75] Inventors: Donald Metcalf; Nicos Antony Nicola; Andrew Wallace Boyd; Judith Eleanor Layton; Kaye Wycherley, all of Melbourne, Australia

[73] Assignee: Amrad Corporation Limited, Victoria, Australia

[21] Appl. No.: 411,812

[22] PCT Filed: Oct. 8, 1993

[86] PCT No.: PCT/AU93/00516

§ 371 Date: Jun. 2, 1995

§ 102(e) Date: Jun. 2, 1995

[87] PCT Pub. No.: WO94/09149

PCT Pub. Date: Apr. 28, 1994

Related U.S. Application Data

[63] Continuation-in-part of Ser. No. 834,534, Aug. 10, 1990, abandoned.

[30] Foreign Application Priority Data

Oct. 9, 1992 [AU] Australia .................... PL-5217

[51] Int. Cl.$^6$ .................. A61K 39/395; A61K 39/40; A61K 39/42; C07K 16/00
[52] U.S. Cl. .................. 424/133.1; 424/141.1; 424/143.1; 435/326; 435/334; 530/388.22
[58] Field of Search ............ 424/133.1, 141.1, 424/143.1; 530/388.22; 435/326, 334

[56] References Cited

U.S. PATENT DOCUMENTS 5,322,838  6/1994  Silberstein et al. .

FOREIGN PATENT DOCUMENTS

| 61896/90 | 3/1991 | Australia . |
|---|---|---|
| WO 91/02063 | 2/1991 | WIPO . |
| WO 94/11404 | 5/1994 | WIPO . |

OTHER PUBLICATIONS

Nicola, N. A. et al., "Neutralizing and Nonneutralizing Monoclonal Antibodies to the Human Granulocyte-Macrophage Colony-Stimulating Factor Receptor α-Chain." *Blood* 82(6):1724–1731 (1993).

Baldwin et al., "Nonhematopoietic Tumor Cells Express Functional GM–CSF Receptors." *Blood* 73:1033–37 (Mar. 1989).

Begley et al., "Primary Human Myeloid Leukemia Cells: Comparative Responsiveness to Proliferative Stimulation by GM–CSF or G–CSF and Membrane Expression of CSF Receptors." *Leukemia* 1:1–8 (Jan. 1987).

Crosier et al., "Granulocyte–Macrophage Colony–Stimulating Factor." *Human Cytokines: Handbook for Basic and Clinical Research*, Aggarwal and Gutterman, eds., Blackwell, Oxford, pp. 238–252 (1992).

Gasson, J.C., "Molecular Physiology of Granulate–Macrophage Colony–Stimulating Factor." *Blood* 77(6):1131–45 (Mar. 15, 1991).

Gearing et al., "Expression Cloning of a Receptor for Human Granulocyte–Macrophage Colony–Stimulating Factor." *Embo J.* 8(12):3667–76 (1989).

Gough and Nicola, "Granulocyte–Macrophage Colony–Stimulating Factor." *Colony–Stimulating Factors: Molecular and Cellular Biology*, Dexter et al., eds. Marcel Dekker Inc., NY, pp. 111–153 (1990).

Grant & Heel, "Recombinant Granulocyte–Macrophage Colony–Stimulating Factor (rGM–CSF): A Review of its Pharmacological Properties and Prospective Role in the Management of Myelosuppression." *Drugs* 43(4):516–560 (Apr. 1992).

Griffin et al., "Effects of Recombinant Human GM–CSF on Proliferation of Clonogenic Cells in Acute Myeloblastic Leukemia." *Blood* 67:1448–53 (May 1986).

Hayashida et al., Molecular Cloning of a Second Subunit of the Receptor for Human Granulocyte–Macrophage Colony–Stimulating Factor (GM–CSF): Reconstitution of a High Affinity GM–CSF Receptor. *PNAS (USA)* 87:9655–59 (Dec. 1990).

Johnson et al., "A Lethal Myeloproliferative Syndrome in Mice Transplanted with Bone Marrow Cells Infected with a Retrovirus Expressing Granulocyte–Macrophage Colony Stimulating Factor." *EMBO J.* 8(2):441–448 (1989).

Kelleher et al., "Binding of Iodinated Recombinant Human GM–CSF to the Blast Cells of Acute Myeloblastic Leukemia." *Leukemia* 2:211–215 (Apr. 1988).

Kitamura et al., "Expression Cloning of the Human IL–3 Receptor cDNA Reveals a Shared β Subunit for the Human IL–3 and GM–CSF Receptors." *Cell* 66:1165–1175 (Sep. 20, 1991).

Kitamura et al., "Reconstitution of Functional Receptors for Human Granulocyte Macrophage Colony–Stimulating Factor (GM–CSF): Evidence that the Protein Encoded by the AIC2B cDNA is a subunit of the Murine GM–CSF Receptor." *PNAS (USA)* 88:5082–86 (Jun. 1991).

Köhler and Milstein, "Continuous Cultures of Fused Cells Secreting Antibody of Predefined Specificity." *Nature* 256:495–97 (Aug. 7, 1975).

(List continued on next page.)

*Primary Examiner*—Anthony C. Caputa
*Assistant Examiner*—Mark Navarro
*Attorney, Agent, or Firm*—Sterne, Kessler, Goldstein & Fox P.L.L.C.

[57] ABSTRACT

The invention relates to monoclonal antibodies specific for the receptor for human granulocyte-macrophage colony stimulating factor (hGM-CSF). The antibodies inhibit the biological activity of hGM-CSF. Methods and compositions for treatment of GM-CSF dependent condition, and methods for screening of selective antagonists to GM-CSF, are also disclosed and claimed.

14 Claims, 12 Drawing Sheets

OTHER PUBLICATIONS

Lang et al., "Transgenic Mice Expressing a Hemopoietic Growth Factor Gene (GM–CSF) Develop Accumulations of Macrophages, Blindness, and a Fatal Syndrome of Tissue Damage," *Cell* 51:675–86 (Nov. 20, 1987).

Metcalf et al., "Low–Affinity Placenta–Derived Receptor for Human Granulocyte–Macrophage Colony–Stimulating Factor Can Deliver a Proliferative Signal to Murine Hemopoietic Cells," *PNAS (USA)* 87:4670–4674 (Jun. 1990).

Nicola and Cary, "Affinity Conversion of Receptors for Colony Stimulating Factors: Properties of Solubilized Receptors," *Growth Factors* 6:119–129 (1992).

Nicola and Metcalf, "Binding, Internalization and Degradation of $^{125}$I–Multipotential Colony–Stimulating Factor (Interleukin–3) by FDCP–1 Cells," *Growth Factors* 1:29–39 (1988).

Onetto–Pothier et al., "Characterization of Granulocyte–Macrophage Colony–Stimulating Factor Receptor on the Blast Cells of Acute Myeloblastic Leukemia," *Blood* 75:59–66 (Jan. 1, 1990).

Tavernier et al., "A Human High Affinity Interleukin–5 Receptor (IL5R) is Composed of an IL–5 Specific α Chain and a β Chain Shared with the Receptor for GM–CSF," *Cell* 66:1175–84 (Sep. 20, 1991).

Bolton and Hunter, "The Labelling of Proteins to High Specific Radioactivities by Conjugation to a $^{125}$I–Containing Acylating Agent," *Biochem. J.* 133:529–539 (1973).

Brown et al., "Two Neutralizing Monoclonal Antibodies Against Human Granulocyte–Macrophage Colony–Stimulating Factor Recognize the Receptor Binding Domain of the Molecule," *J. Immunol.* 144:2184–2189 (Mar. 15, 1990).

Kohler and Milstein, "Derivation of Specific Antibody–Producing Tissue Culture and Tumor Lines by Cell Fusion," *Eur. J. Immunol.* 6:511–519 (1976).

Goring, Monoclonal Antibodies: Principle and Practice Second Edition Academic Press pp. 124–133 1986.

Oi et al BioTechniques vol. 4 No. 3 pp. 214–221, 1986.

MONOCLONAL ANTIBODY TO HUMAN GRANULOCYTE MACROPHAGE COLONY STIMULATING FACTOR

This application is a continuation of the national phase of PCT/AU93/00516, filed Oct. 8, 1993, published as WO94/09149 Apr. 28, 1994, which is a continuation in part of U.S. appl. Ser. No. 07/834,534, filed Aug. 10, 1990, now abandoned.

This invention relates to monoclonal antibodies specific for the receptor for human granulocyte-macrophage colony stimulating factor (hGM-CSF), and to compositions and methods utilizing these antibodies.

BACKGROUND AND PRIOR ART

Granulocyte-macrophage colony-stimulating factor (GM-CSF) is a growth and differentiation factor for a variety of haemopoietic progenitor cells (including those for neutrophils, macrophages, eosinophils, megakaryocytes and erythroid cells) and can also functionally activate mature neutrophils, eosinophils and macrophages (Metcalf, D., *The Molecular Control of Blood Cells*, Harvard University Press, Cambridge, Mass. (1988); Gough and Nicola, "Granulocyte-Macrophage Colony-Stimulating, Factor," In *Colony-Stimulating Factors: Molecular and Cellular Biology*, Dexter et al., eds, Marcel Dekker Inc., NY, pp. 111–153 (1990); Gasson, J. C., *Blood:*77:1131–1145 (1991); Crosier et al., "Granulocyte-Macrophage Colony-Stimulating Factor," In *Human Cytokines: Handbook for Basic and Clinical Research*, Aggarwal and Gutterman, eds., Blackwell, Oxford, pp. 238–252 (1992)). All of the actions of GM-CSF are thought to be mediated through the interaction of GM-CSF with specific cell surface receptors. These receptors consist of a specific α-chain (PCT/AU90/00342, published as WO 91/02063) (Gearing et al., Embo J. 8:3667–3676 (1989)), which binds GM-CSF with low-affinity, and a common β-chain, which by itself does not bind GM-CSF with detectable affinity, and is shared by the α-chains for the interleukin-3 and interleukin-5 receptors (Kitamura et al., *Cell* 66:1165–1174 (1991); Tavernier et al., *Cell* 66:1175–1184 (1991)). The α–β complex generates high-affinity binding sites for GM-CSF, and is required for cell signalling (Kitamura et al., PNAS (USA) 88:5082–5086 (1991)). However, the mechanism of conversion of the low affinity receptor to high affinity is not yet understood.

Since murine models of excess GM-CSF production (Lang et al., *Cell* 51:675–686 (1987); Johnson et al., *EMBO J.* 8:441–448 (1989)) have indicated that a variety of disease states can result from over-production of GM-CSF and consequent macrophage accumulation, and since clinical trials of GM-CSF have indicated that some disease states can be exacerbated by the action of GM-CSF (Grant and Heel, Drug 43:516–560 (1992)), we believe that antibodies that inhibit GM-CSF action may have clinical utility. Moreover, since several human myeloid leukemias have been shown both to possess GM-CSF receptors and to respond to GM-CSF by proliferation (Begley et al., *Leukemia* 1:1–8 (1987); Griffin et al., *Blood* 67:1448–1453 (1986); Kelleher et al., *Leukemia* 2:211–215 (1988); Onetto-Pothier et al., *Blood* 75:59–66 (1990)); Baldwin et al., *Blood* 73:1033–1037 (1989)), we believe that such antibodies could be used to suppress leukaemic cell proliferation or to target leukemic cells for antibody-mediated killing. Finally we believe that identification of the antibody epitope on the GM-CSF receptor α-chain recognized by neutralizing antibody will aid in the design of selective peptide and non-peptide antagonists of GM-CSF action.

We have generated a panel of monoclonal antibodies that specifically recognize the human GM-CSF receptor α-chain, and one of these inhibits the capacity of GM-CSF to bind to its cellular receptor and to biologically stimulate cells that bear GM-CSF receptors. Surprisingly, this inhibition occurs on cells that bear either the α-chain of the receptor alone (FD-A5 cells), or which bear the high-affinity α–β complex (AML 193 cells, human bone marrow cells).

SUMMARY OF THE INVENTION

According to a first aspect, the invention provides monoclonal antibodies specific for hGM-CSF receptor, which antibodies have the ability to inhibit the biological activity of hGM-CSF. Preferably the monoclonal antibodies of the invention are able to bind to both the high affinity and to the low-affinity GM-CSF receptor.

In a preferred embodiment, the monoclonal antibody is KI-2B7-17-A.

According to a second aspect, the invention provides hybridoma cell lines producing these monoclonal antibodies.

According to a third aspect, the invention provides therapeutic compositions comprising a monoclonal antibody according to the invention, together with a pharmaceutically acceptable carrier.

According to a fourth aspect of the invention, there is provided a method of treatment of a GM-CSF dependent condition, comprising the step of administering to a patient in need of such treatment an effective amount of a monoclonal antibody according to the invention, optionally together with a pharmaceutically-acceptable carrier. It is contemplated that methods of treatment either by suppression of leukemic cell proliferation, or by targeting of leukemic cells for antibody-mediated killing are within the scope of the invention. This method of the invention is applicable to both acute and chronic myeloid leukemia, and to other leukemias which are influenced by GM-CSF.

In a particularly preferred embodiment, the method of the invention provides a method of mitigation of the side-effects of treatment with GM-CSF, comprising the step of administering to a patient in need of such treatment an effective amount of a monoclonal antibody of the invention, optionally together with a pharmaceutically-acceptable carrier.

In a further aspect, the invention provides a method of screening of selective antagonists to GM-CSF, comprising the step of utilizing an antibody of the invention to identify the specific epitope on GM-CSF receptor recognized by said antibody, and testing putative antagonists of GM-CSF action for ability to bind to said epitope. The antagonists may be either peptides, or non-peptide molecules.

Using the methods described herein, screening of a relatively small number of hybridoma clones revealed 15 candidate clones, of which one surprisingly produced a monoclonal antibody having inhibitory activity against high-affinity hGM-CSF receptor. Thus hybridoma clones having the required specific activity can be produced at high frequency, and it is considered that the skilled person would readily be able to utilize the methods described herein in order to produce neutralizing monoclonal antibodies.

Similarly, methods for producing "humanized" forms of monoclonal antibodies, or for producing antigen-binding fragments of monoclonal antibodies, by the use of genetic engineering techniques are well-known in the art. Thus such humanized forms or antigen-binding fragments are also to be clearly understood to be within the scope of the invention.

DETAILED DESCRIPTION OF THE INVENTION

The invention will now be described by way of reference only to the following non-limiting examples, and to the accompanying drawings, in which FIG. 1 shows the results of immunodepletion assays in which the ability of monoclonal antibodies to deplete solubilized hGM-CSF receptor α-chain from solution was tested;

FIG. 2 summarizes results of immunofluroescence detection of hGM-CSF receptor α-chain on FDA5 cells;

Figure 5A:
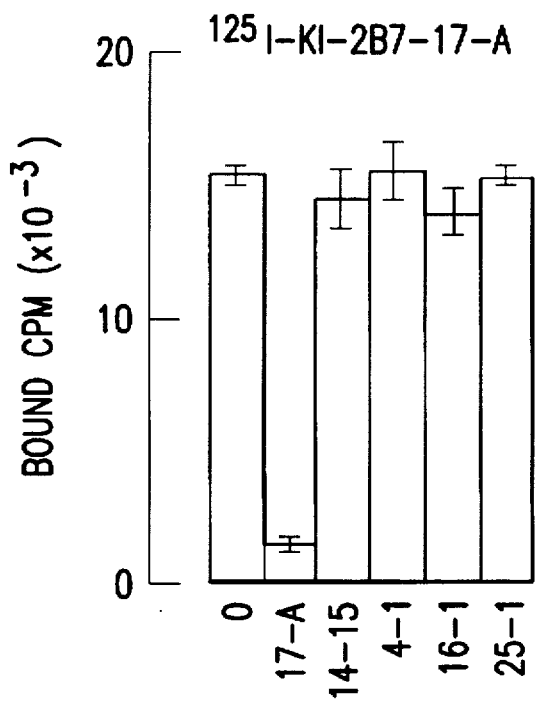
Figure 6A:
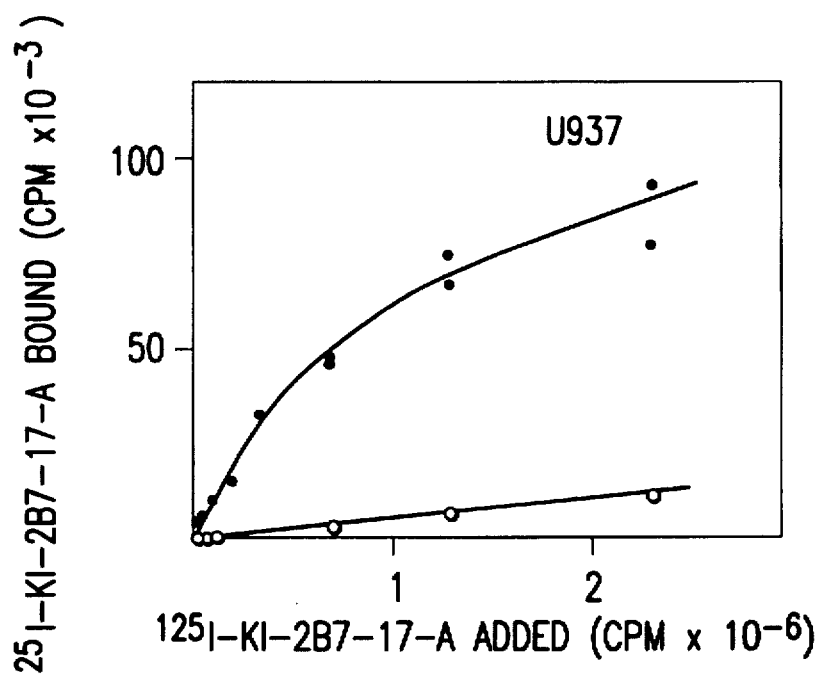
Figure 6B:
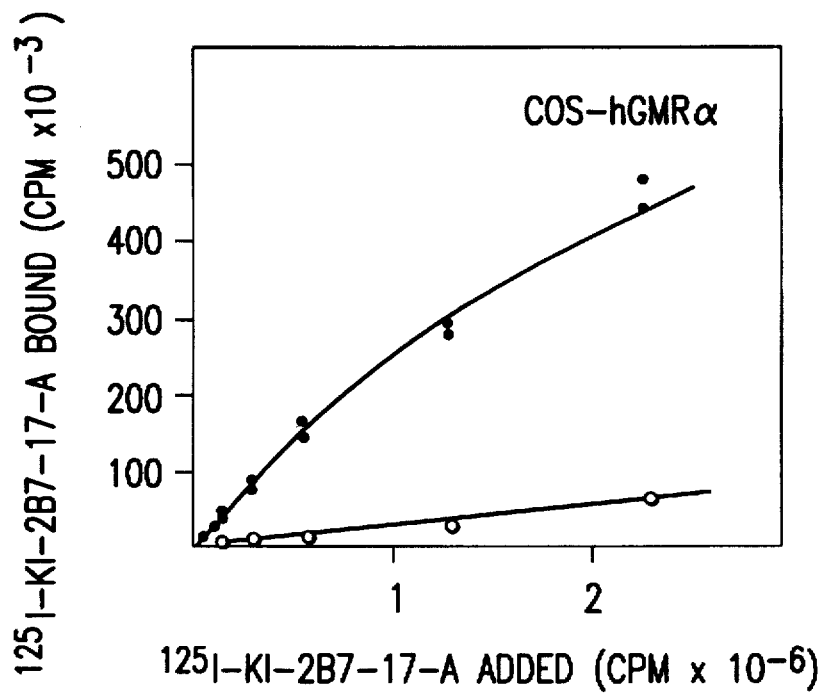
Figure 6C:
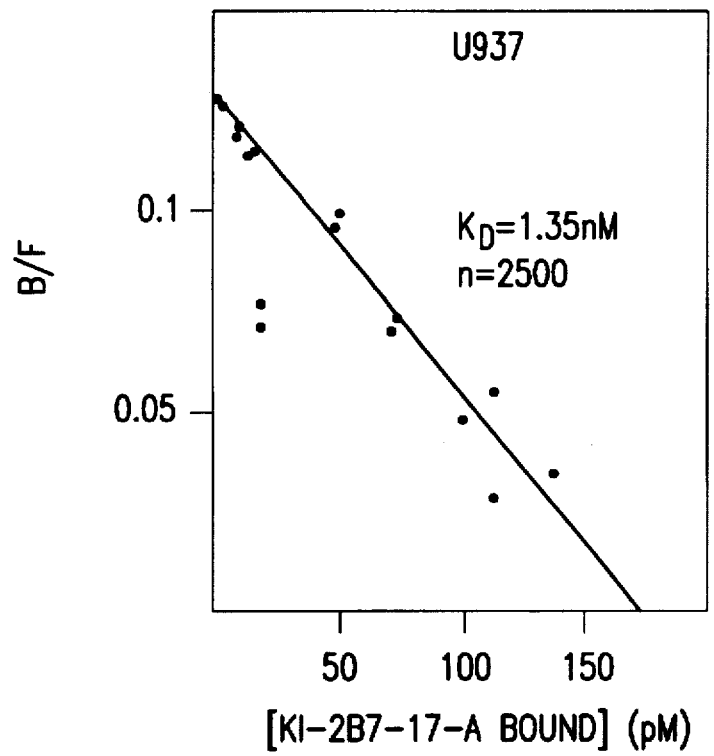
Figure 6D:
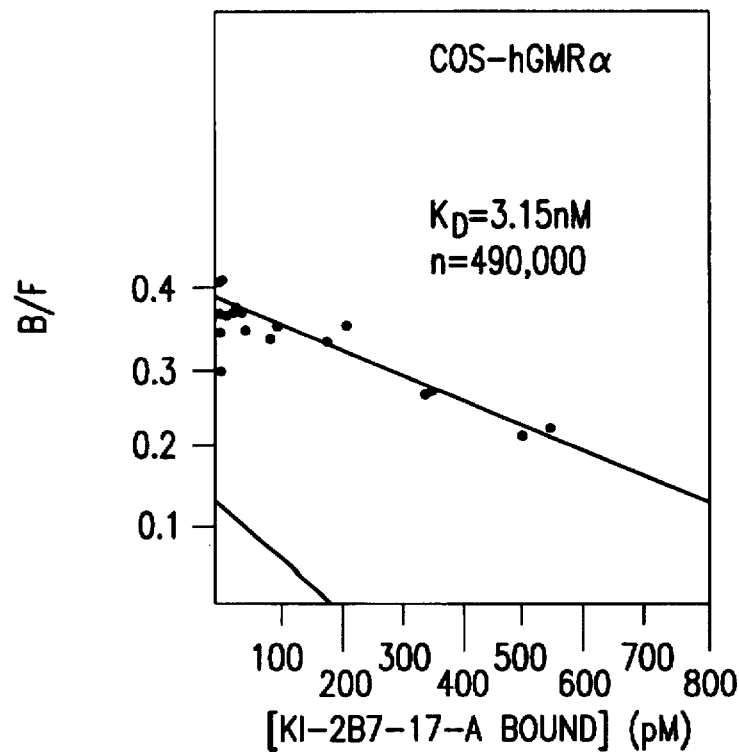
Figure 7A:
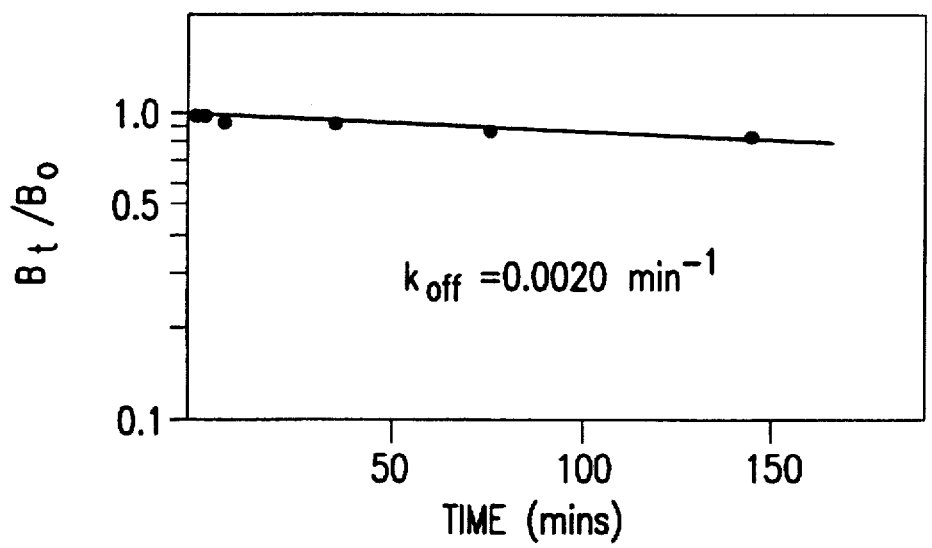

FIGS. 5A and B show that only one of the five monoclonal antibodies tested had the ability to directly inhibit binding of hGM-CSF to solubilized receptor;

FIGS. 6A and 6B shows results of binding studies to determine the binding affinity of an antibody of the invention to hGM-CSF receptor;

FIGS. 6C and 6D shows corresponding Scatchard plots;

FIGS. 7A and B show the kinetic association and dissociation rates of binding of an antibody of the invention to hGM-CSF receptor.

Figure 8A:
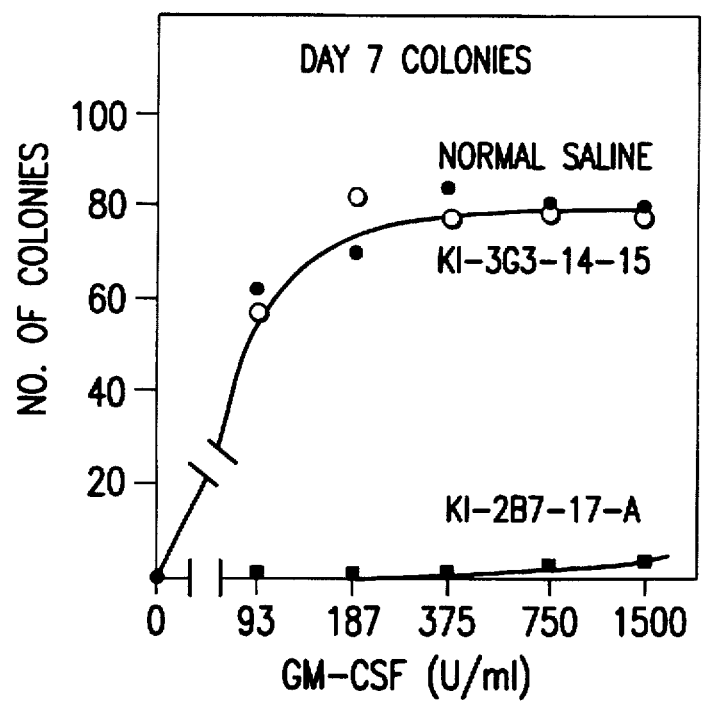
Figure 9A:
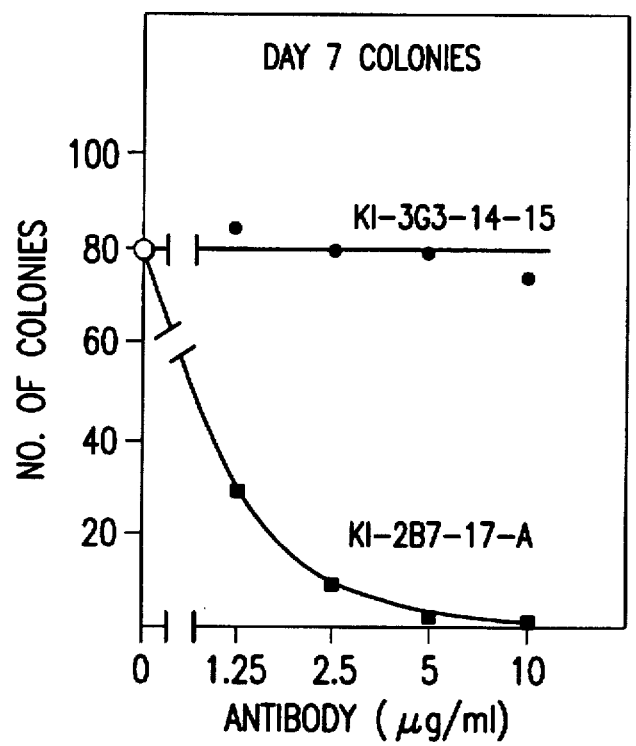
Figure 10:
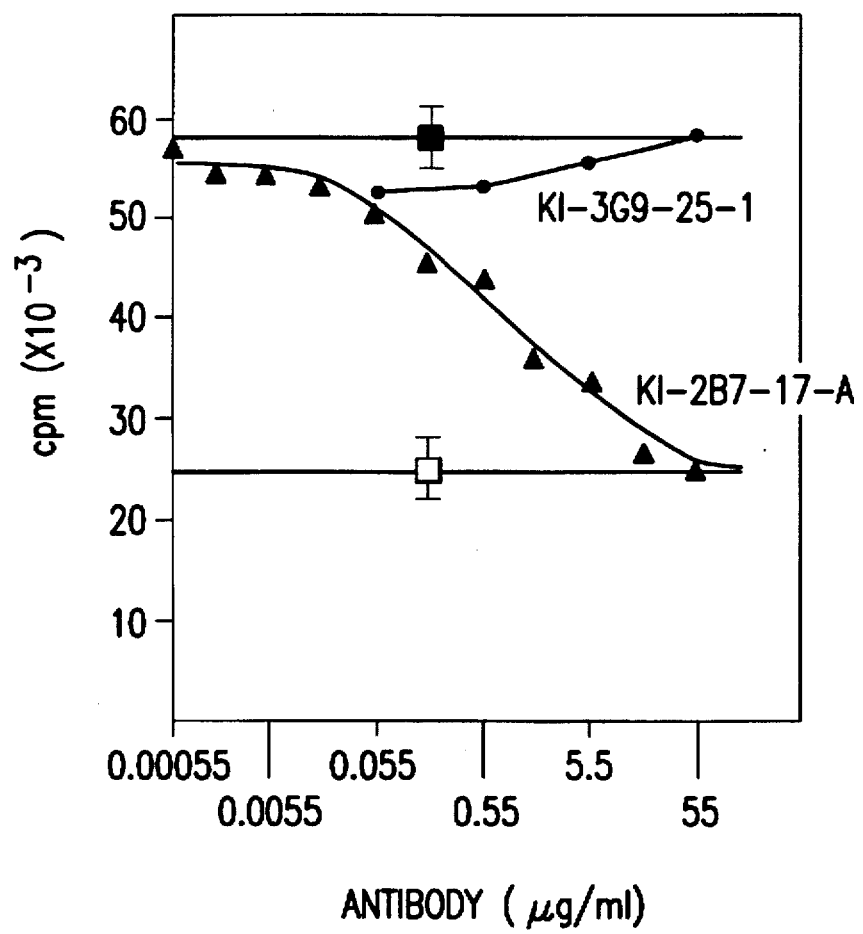
Figure 11A:
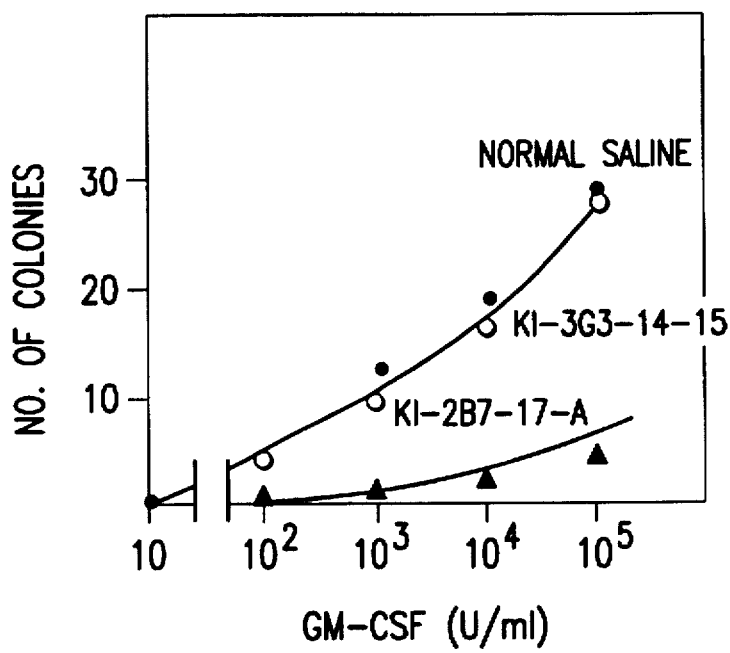

FIGS. 8A and B show inhibition by an antibody of the invention of colony formation by human bone marrow cells in response to hGM-CSF;

FIGS. 9A and B show that this inhibition is dose-dependent;

FIG. 10 illustrates the ability of an antibody of the invention to inhibit growth in vitro of an hGM-CSF dependent cell line; and FIGS. 11A and B show inhibition of stimulation by hGM-CSF of a cell line transfected with hGM-CSF receptor α-chain.

In the following examples, the invention is described in detail with reference to monoclonal antibody produced by the hybridoma cell line KI-2B7-17-A. A sample of this hybridoma cell line was deposited under the Budapest Treaty in the Public Health Laboratory Service Centre for Applied Microbiology and Research European Collection of Animal Cell Cultures, Porton Down, Salisbury, Wiltshire, SP4 0JG, U.K. on 23 Sep. 1992, under Accession Number 92092317.

Abbreviations used herein are as follows:

| DME | Dulbecco's modified Eagle's medium |
| FCS | foetal calf serum |
| FITC | Fluorescein isothiocyanate |
| GM-CSF | granulocyte-macrophage colony stimulating factor |
| ICAM-1 | Intercullular adhesion molecule-1 |
| SAMIg | Sheep anti-mouse immunoglobulin |

All of the cell lines referred to herein are publicly available, or have been previously described in the literature.

EXAMPLE 1

Hybridoma Production

In initial studies, mouse FDC-P1 cells transfected with the human GM-CSF receptor α-chain (FDA5 cells) (Metcalf et al., PNAS (USA) 8:4670–4674 (1990)) were injected into syngeneic BALB/c recipients, in the expectation that this would result in more specific immune responses. No successful fusions resulted with this protocol. Since our prior observations had shown that allogeneic responses enhanced the immune response to other cell surface antigens, we immunized CBA/J mice with allogenic FDA5 cells. The mice received weekly intraperitoneal injections of 2–3×10$^7$ viable FDA5 cells for four weeks, and sera were assayed in the immunodepletion assay (see below). The mice were then rested for at least four weeks before a final immunization. Four days after this final boost the animals were killed by cervical dislocation and the spleens removed. Single cell suspensions were prepared and washed in serum-free Dulbecco's modified Eagle's medium (DME). The spleen cells (Köhler and Milstein Eur. J. Immunol. 6:511–519 (1976)) were fused with NS-1 myeloma cells in the presence of 50% (w/v) polyethylene glycol 4000 (Boehringer-Mannheim).

The cells were gently resuspended in DME/15% (v/v) fetal calf serum (FCS) 10% (v/v) conditioned medium from the P33D18 macrophage cell line (as a source of interleukin-6), and cultured in 96 well Falcon microwell flat bottom trays at 2×10$^5$ cells per well. The cells were fed with a standard selective medium containing hypoxanthine, aminopterin and thymidine (HAT medium) after overnight culture, and thereafter every three days. After 7–14 days, developing hybridoma clones were observed in the wells and supernatants were harvested for testing.

EXAMPLE 2

Screening of Hybridoma Clones a) Analysis of COS 7 Cell Transfectants by Immunofluorescence.

COS 7 cells (ATCC CRL 9589) were electroporated with expression plasmids encoding the α-chain of the human GM-CSF receptor (Gearing et al., Embo J. 8:3667–3676 (1989)) or the cell surface molecule ICAM-1 (Simmons et al Nature 331:624–627 (1976)). After three days the cells were harvested, washed and analyzed with candidate hybridoma supernatants by indirect immunofluorescence. Briefly, 10$^6$ cells were incubated with 50 μl of culture supernatant for 30 min at 4° C. The cells were washed, resuspended in an appropriate dilution of FITC-(Fab$_2$)' fragments of sheep anti-mouse immunoglobulin antibody (FITC SAMIg) (DDAF, Silenus), and held on ice for 30 min at 4° C. The cells were washed and then fixed in 1% formalin in phosphate-buffered saline (PBS). The samples were examined by fluorescence microscopy and 35 putative positives (GMR$^+$, ICAM$^-$) identified from a total of 390 wells. The cells from these wells were expanded to generate further supernatants for testing and to provide cells for recloning and cryopreservation. Fifteen clones remained positive by immunofluorescence and were further selected by screening in immunodepletion assays (see below).

(b) Immunodepletion Assays.

COS 7 cells that had been electroporated with the human GM-CSF receptor α-chain cDNA in the CDM8 vector 72 hours previously were lysed, and membranes purified as previously described (Nicola and Cary Growth Factors 6:119–129 (1992)). The membranes were extracted with 1% Triton X-100, centrifuged at 200,000 g for 15 min and the supernatant retained as solubilized GM-CSF receptor α-chain.

Solubilized GM-CSF receptor α-chain (50 μl) was pre-incubated with hybridoma supernatant (100 μl), sheep anti-mouse immunoglobulin (100 μl of a 1/100 dilution) and protein-G Sepharose (100 μl of a 1/5 suspension) in a final volume of 400 μl of Hepes-buffered (20 mM, pH 7.4) RPMI medium containing 10% (v/v) fetal calf serum for 60 min at 23° C. with rotation. Tubes were then centrifuged at 14,000 g for 10 sec and the supernatants recovered.

Supernatants (50 μl aliquots) were incubated with $^{125}$I-human GM-CSF (10 μl, ~200,000 cpm, specific radioactivity 30,000 cpm/ng) in duplicate, with or without unlabelled human GM-CSF (10 μl of 50 μg/ml) and Concanavalin A-Sepharose 4B (30 μL of a ¼ suspension in 0.1M sodium acetate buffer pH 6.0), for 60 min at 23° C. with rotation. The incubation mixture was then layered over 180 μl of fetal calf serum in small centrifuge tubes, centrifuged at 14,000 g for 10 sec and the pellet removed by cutting the tube with a scalpel blade. Specific binding in these pellets was calculated as the binding (cpm) without unlabelled GM-CSF minus the binding in the presence of unlabelled GM-CSF.

The presence of monoclonal antibody against the human GM-CSF receptor α-chain was detected by the ability of the appropriate hybridoma supernatant to deplete soluble human GM-CSF receptor α-chain in the preincubation step (relative to control hybridoma supernatant or antibody), as revealed by a reduction in the specific binding of $^{125}$I-human GM-CSF detected in the subsequent incubation.

EXAMPLE 3

Direct Binding Inhibition Assays

Solubilized human GM-CSF receptor α-chain (50 μl), monoclonal antibody or hybridoma supernatant (10 μl), $^{125}$I-human GM-CSF (10 μl, ~200,000 cpm), and Concanavalin A-Sepharose 4B (30 μl of a ¼ suspension) with or without unlabelled human GM-CSF (10 μl of 50 μl/ml), in a total volume of 110 μl of 0.1M NaAcetate buffer pH 6.0 were incubated at 23° C. for 60 min with rotation, and specific binding was determined as described above.

EXAMPLE 4

Isotype Determination of Monoclonal Antibodies

Supernatants from positive hybridoma clones were isotyped using the Amersham Isotyping Kit (Amersham, Buckinghamshire, England). Monoclonal antibody KI-2B7-17A, along with several other monoclonals, was found to be of the IgG2a type.

EXAMPLE 5

Purification of Monoclonal Antibodies

Individual hybridoma cell lines were expanded to 10 liters of culture volume and the supernatants harvested and concentrated 16-fold. The concentrated supernatants were loaded on to a protein-A-Sepharose CL-4B column (5 ml) (Pharmacia, Uppsala, Sweden), and the column was washed extensively with phosphate (20 mM, pH 7.4) buffered 0.15M saline (PBS) until the absorbance at 280 nm was negligible. The column was then eluted with 0.1M glycine HCl buffer pH 3.0 and fractions collected into ⅒ volume of 1.0M Tris HCl pH 8. The eluates were concentrated and dialyzed extensively against PBS before use.

EXAMPLE 6

Radiolabeling of Monoclonal Antibodies

Monoclonal antibodies were radioiodinated with $^{125}$I either by the modified iodine monochloride method described previously (Nicola and Metcalf, Growth Factors 1:29–39 (1988)), or by the use of $^{125}$I-Bolton-Hunter reagent (Bolton and Hunter Biochem. J. 133–529–539 (1973)). Monoclonal antibody KI-2B7-17-A only retained binding activity when iodinated using the Bolton-Hunter reagent, so direct binding studies were performed with this form of the iodinated antibody (specific radioactivity 50,000 cpm/ng).

EXAMPLE 7

Immunodepletion Studies

Figure 1:
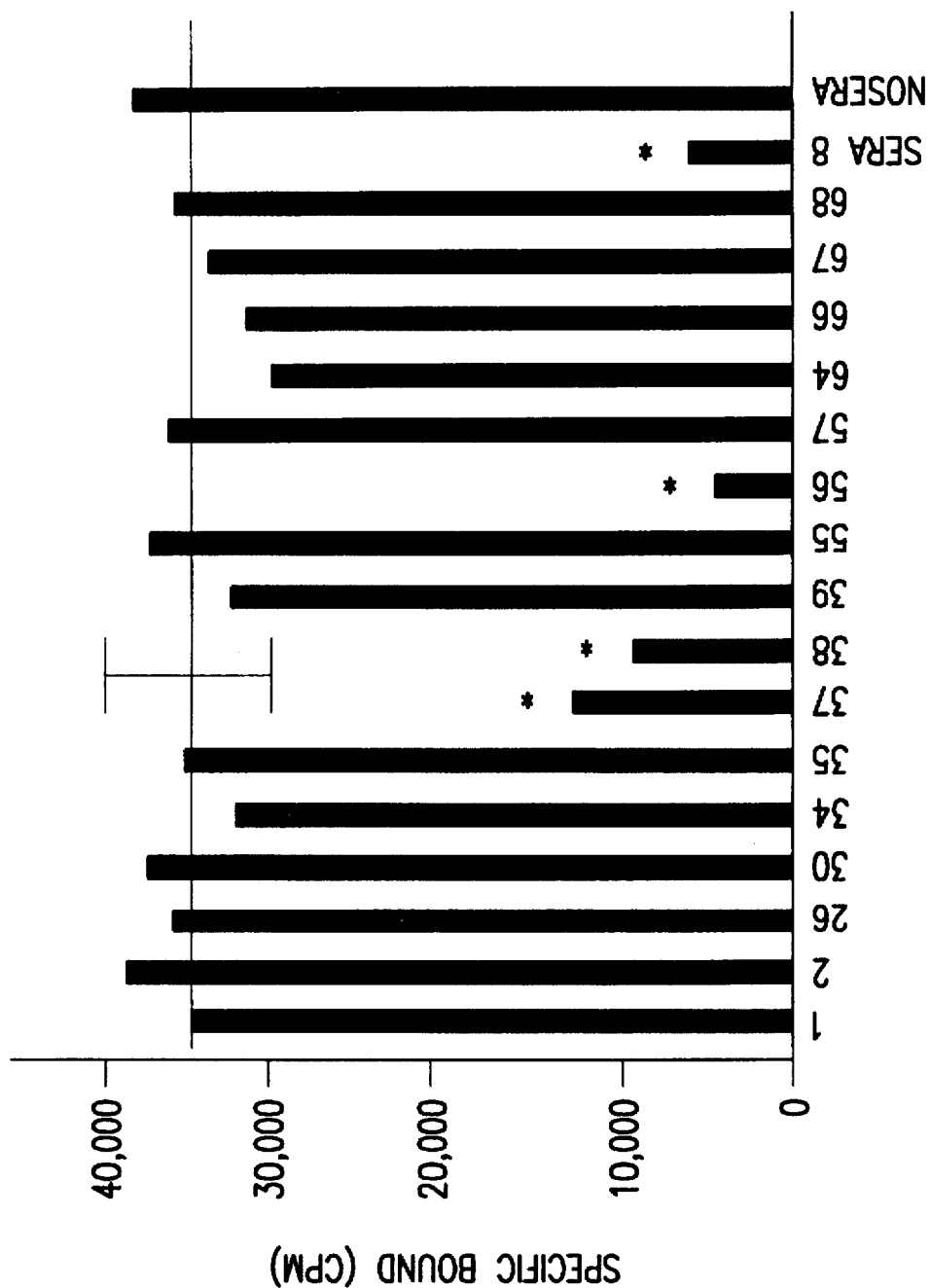

FIG. 1 shows the capacity of randomly selected hybridoma supernatants to deplete solubilized human GM-CSF receptor α-chain from solution. After immunodepletion, the solution was tested for residual specific binding of $^{125}$I-human GM-CSF. Mean specific cpm bound and standard deviation are shown by the horizontal line and error bar in FIG. 1 for solutions that had not been immunodepleted. Most hybridoma supernatants did not reduce the specific binding, but supernatants 37, 38 and 56 clearly caused a marked reduction in specific binding, indicating that they contained antibodies that could recognize the human GM-CSF receptor α-chain. In addition the serum from immunized mouse number 8 also contained antibodies which recognized the receptor. This assay allowed the identification of five purified monoclonal antibodies (KI-3G9-25-1, KI-3G3-14-15, KI-2B7-17-A, K3-2E9-4-1 and K3-2C7-16-1), each derived from double cloned hybridoma cell lines that recognized the human GM-CSF receptor α-chain.

EXAMPLE 8

Immunological Detection of Human GM-CSF Receptor α-chain on FDA5 Cells

Figure 2:
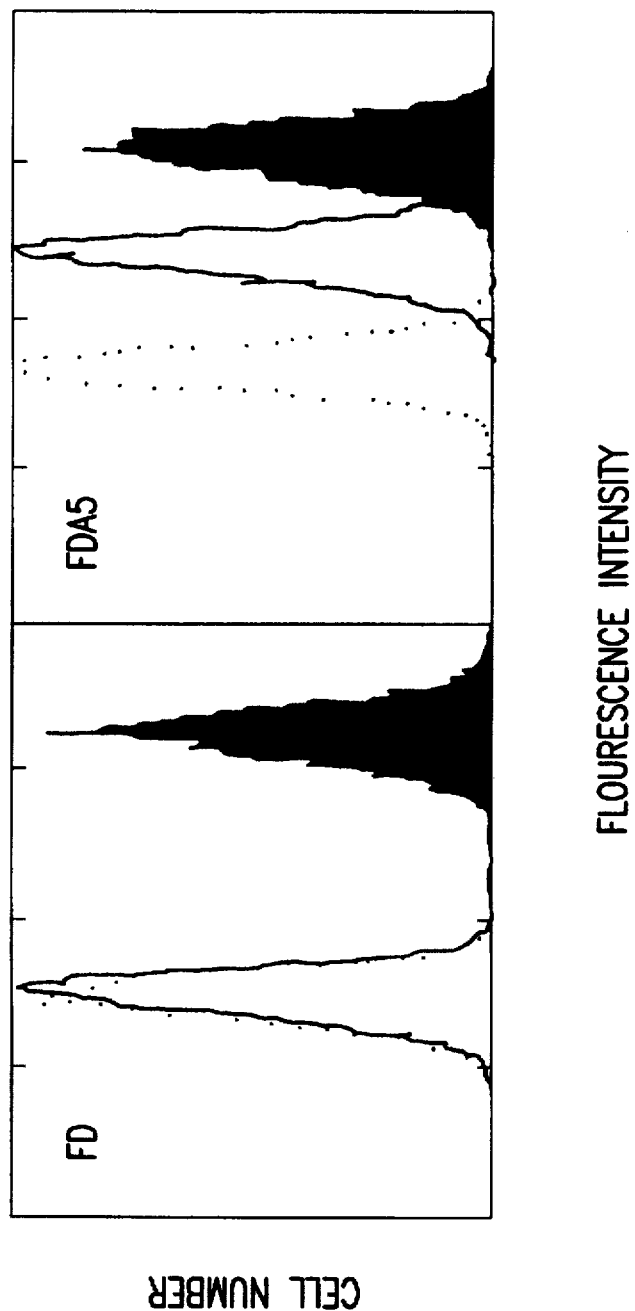

FIG. 2 shows that FDA5 cells (Metcalf et al., PNAS (USA) 8:4670–4674 (1990)), but not parental FDC-P1 (FD) cells (Metcalf et al., supra.), showed significant fluorescence above background when stained with the monoclonal antibodies KI-2B7-17-A and FITC SAMIg and then subjected to flow cytometry (solid line, unfilled). The positive control, indicated in black, shows fluorescence with anti-H2D antibodies. The dotted profile represents fluorescence of cells treated with FITC-SAMIg in the absence of test antibody.

EXAMPLE 9

Direct Binding Inhibition Studies

Figure 3:
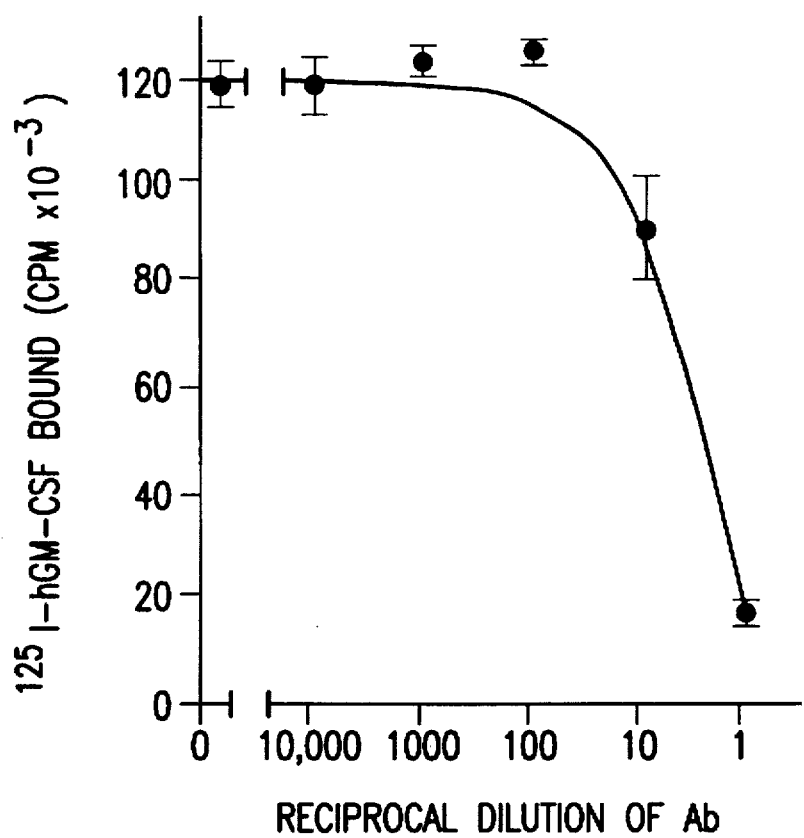
FIG. 3 shows results of direct binding inhibition studies, showing dose-dependent inhibition by a representative antibody of the invention of binding of GM-CSF to receptor.

FIG. 3 shows that when monoclonal antibody KI-2B7-17-A was co-incubated with solubilized human GM-CSF receptor α-chain and $^{125}$I-human GM-CSF (with no prior immunodepletion step), the antibody directly interfered with $^{125}$I-GM-CSF binding to the receptor, as evidenced by the dose-dependent inhibition of the amount of $^{125}$-GM-CSF bound to the receptor which was observed.

Figure 4:
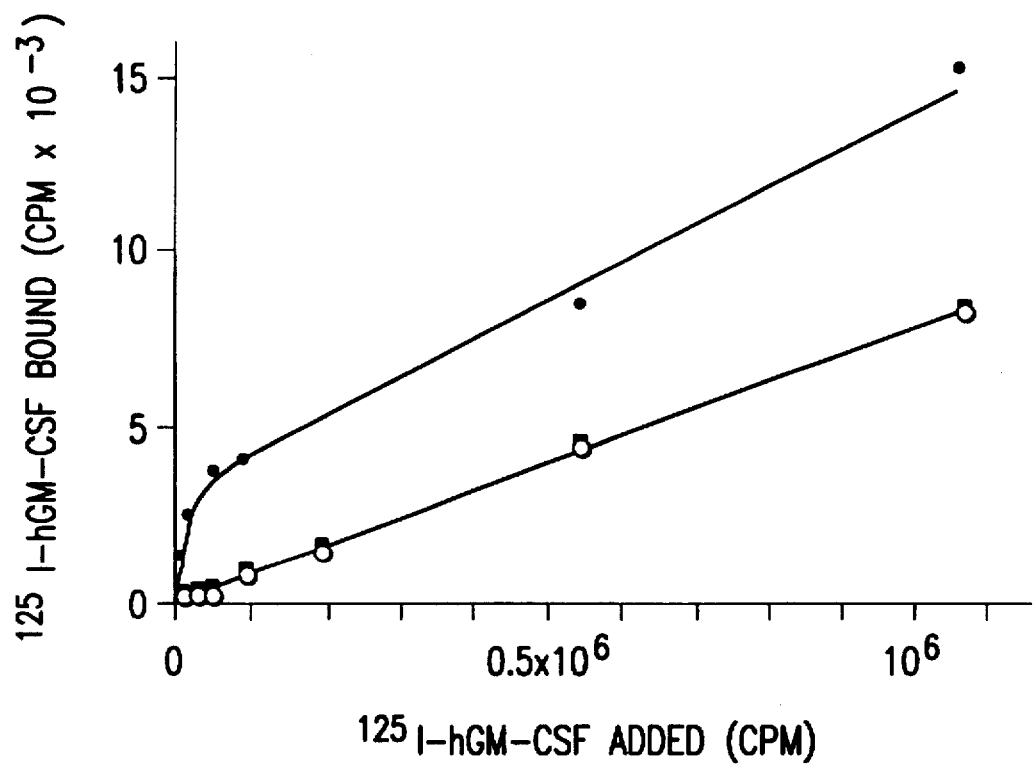
FIG. 4 shows suppression of specific binding of GM-CSF to receptors by the antibody of the invention.

This antibody also completely suppressed specific binding of $^{125}$I-GM-CSF to GM-CSF receptors on cells of the HL60 promyelocytic leukemic cell line, which had been induced to differentiate by exposure to 1% dimethylsulphoxide for 5 days, as shown in FIG. 4.

When KI-2B7-17-A antibody (10 μg/ml) was co-incubated with the cells and $^{125}$I-human GM-CSF (0–10$^6$ cpm, 0–3 ng/ml) it reduced the specific binding (filled squares) to the same extent as unlabelled human GM-CSF (5 μg/ml) (open circle).

Figure 5B:
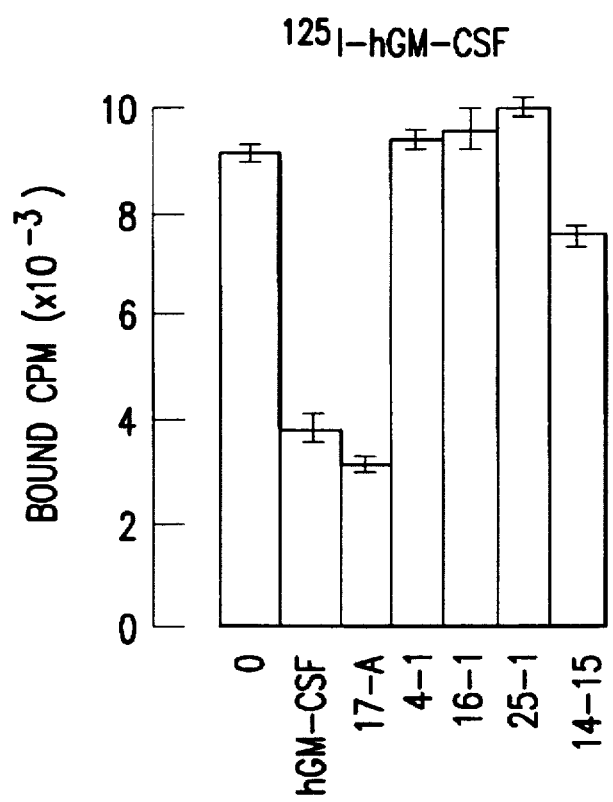

FIG. 5 shows that monoclonal antibody KI-2B7-17-A was unique amongst the five purified monoclonal antibodies directed against the human GM-CSF receptor α-chain, in that it directly inhibited the binding of $^{125}$I-human GM-CSF to solubilized receptor. This suggested that KI-2B7-17-A recognized a unique epitope on the GM-CSF receptor α-chain which is involved in GM-CSF binding. This was confirmed by showing that only unlabelled KI-2B7-17-A, and not the other four monoclonal antibodies, could compete for the direct binding of $^{125}$I-KI-2B7-17-A to human GM-CSF receptor α-chain expressed on COS cells (FIG. 5).

EXAMPLE 10

Direct Binding of KI-2B7-17-A to Human GM-CSF Receptor

In order to demonstrate the direct binding of the KI-2B7-17-A antibody to human GM-CSF receptor and determine its binding affinity, the antibody was iodinated using $^{125}$I-Bolton-Hunter reagent. Increasing amounts of $^{125}$I-KI-2B7-17-A were incubated with U937 human monocytic cells (ATCC CRL 1593) as a source of natural high-affinity human GM-CSF receptor, or with COS cells transfected with human GM-CSF receptor α-chain, and specific binding was determined as the difference in cpm bound in the presence or absence of unlabeled KI-2B7-17-A (12 μg/ml). FIGS. 6A and 6B shows the binding isotherms generated at 4° C., and their transformation into Scatchard plots (20) is shown in FIGS. 6C and 6D. The binding affinity of the antibody to U937 cell GM-CSF receptor was characterized by an equilibrium dissociation constant ($K_D$) of 1.35 nM and 2500 sites/cell. This compares to a $K_D$ of 0.41 nM and site number of 1500 sites/cell for $^{125}$I-human GM-CSF on the same cells (data not shown). A similar affinity of binding of the antibody to transfected COS cells was determined ($K_D$= 3.15 nM), although a much higher number of receptors was detected (490,000/cell). The solid line in FIG. 6D is the same as that in FIG. 6C, drawn to the same scale for comparative purposes. With these affinity constants KI-2B7-17-A should give 50% inhibition at between 0.1–1 μg/ml, and this accords with the observations in example 11.

Figure 7B:
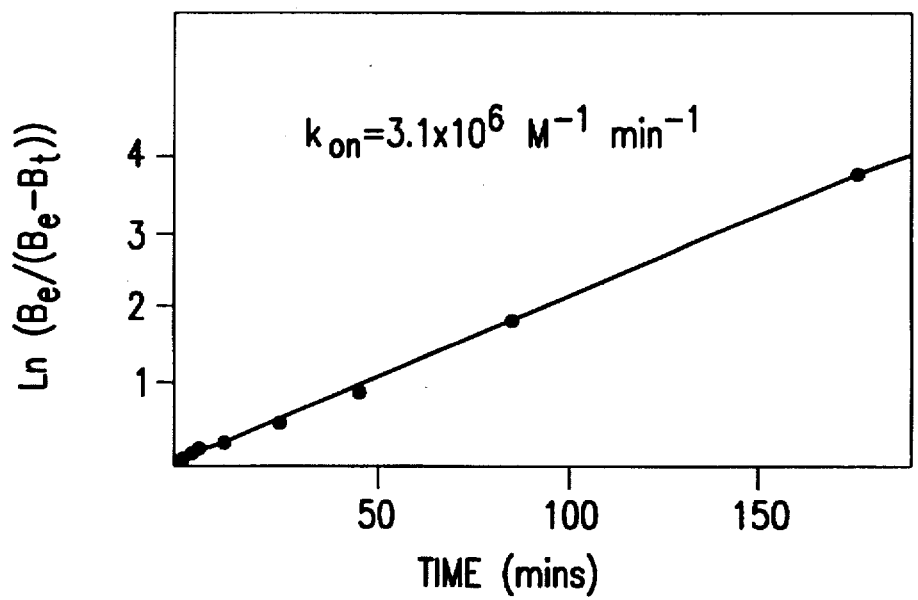

We further characterized the direct binding of $^{125}$I-KI-2B7-17-A antibody to natural human GM-CSF receptor on U937 cells by measuring its rate of association ($k_{on}$) and rate of dissociation ($k_{off}$) from the receptor (FIG. 7). In Part A of this figure, U937 cells (2.2×10$^6$ per point) were incubated with $^{125}$I-KI-2B7-17-A antibody (500,000 cpm/50 μl/point) for at least 1 hr at 4° C. The cells were then rapidly washed and resuspended in binding medium containing 20 μg/ml of unlabeled antibody. At the indicated time points aliquots of cells were removed, and the specifically bound radioactivity remaining determined as described for other figures. $k_{off}$ was determined from the plot in FIG. 7A as 0.002 min$^{-1}$ ($k_{off}$=ln 2/t½). In Part B the same number of U937 cells and $^{125}$I-KI-2B7-17-A antibody were mixed, and aliquots removed at the indicated times at 4° C. to determine specifically bound radioactivity ($B_t$). The data were extrapolated to determine the amount bound at infinite time (Be), and the data plotted as ln[Be/(Be−Bt)] versus time. The slope of the line is $k_{on}$[Antibody]+$k_{off}$, so since the concentration of $^{125}$I-KI-2B7-17-A was known, $k_{on}$ could be calculated as 3.1×10$^6$ M$^{-1}$ min$^{-1}$. The slow dissociation rate of the antibody (0.002 min$^{-1}$) makes it useful as an inhibitor of the GM-CSF receptor.

EXAMPLE 11

Figure 8B:
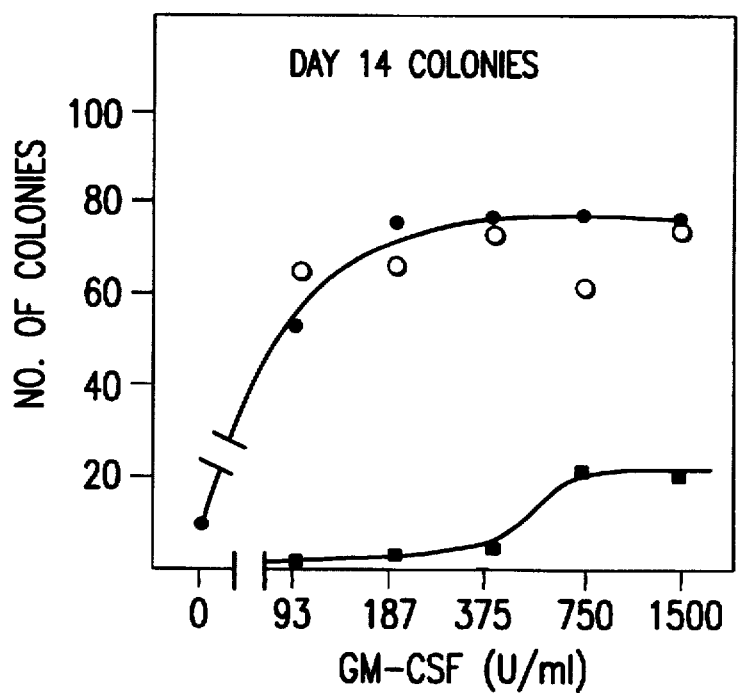
Figure 9B:
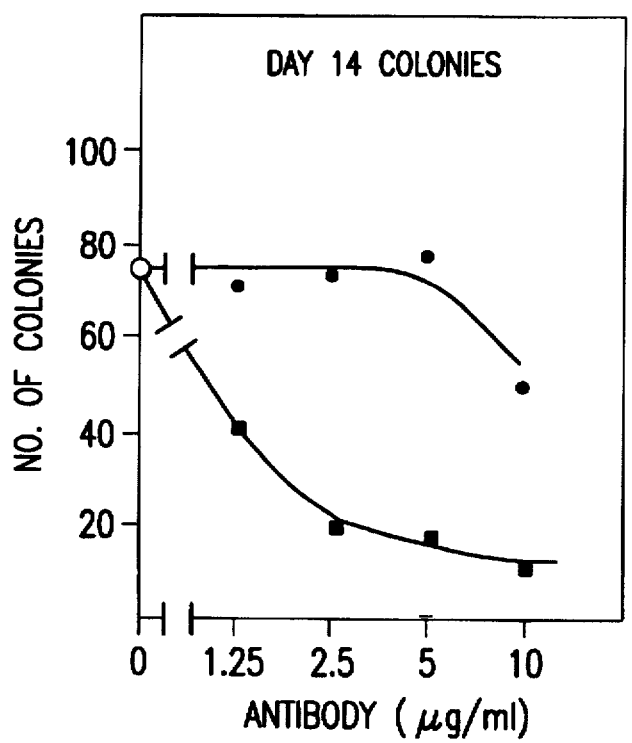

Inhibition of the Biological Action of GM-CSF by Monoclonal and Antibody KI-2B7-17-A Monoclonal antibody KI-2B7-17-A (filled squares), but not the isotype matched monoclonal antibody KI-3G3-14-15 (open circles), which was obtained from a similar fusion and also recognizes the human GM-CSF receptor α-chain, nor saline (closed circles), was able to inhibit colony formation from human bone marrow cells stimulated by human GM-CSF in semisolid agar cultures in vitro (FIG. 8). At 10 μg/ml, KI-2B7-17-A almost completely inhibited colony formation induced by up to 1500 U/ml of GM-CSF when cultures were scored at day 7. A similar but less marked inhibition was seen when cultures were scored at day 14. FIG. 9 shows that the inhibition of colony formation (stimulated by 400 U/ml of GM-CSF) was dependent on the dose of antibody KI-2B7-17-A, with 50% inhibition occurring at about 1 μg/ml and nearly complete inhibition occurring at about 10 μg/ml.

FIG. 10 shows that antibody KI-2B7-17-A also inhibited the growth in vitro of the human GM-CSF-dependent acute monocytic leukemia cell line AML-193 (ATCC CRL 9589), as assessed by the inhibition of incorporation of $^3$H-methyl-thymidine into cellular DNA. 50% inhibition again occurred at 1 μg/ml of antibody, and nearly complete inhibition of GM-CSF-stimulated growth occurred at 10–100 μg/ml. The solid line with a filled square and error bars represents incorporation into cells in the absence of added antibody, while the solid line with open square and error bars represents incorporation in the absence of GM-CSF. No signficant inhibition was observed with the isotype-matched antibody KI-3G9-2S1 (closed circles)

Figure 11B:
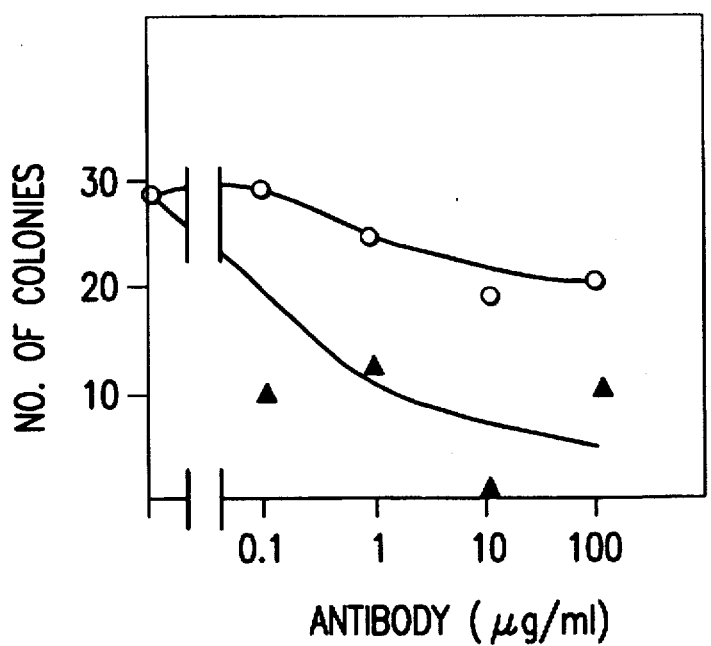

Finally FIG. 11 shows that antibody KI-2B7-17-A inhibited the growth in vitro in semisolid agar cultures of the FD-A5 cells (mouse FDC-P1 cells transfected with human GM-CSF receptor α-chain) stimulated by human GM-CSF, as assessed by colony formation and colony size. Again 50% inhibition occurred at about 1 μg/ml, and nearly complete inhibition occurred by 10 μg/ml. In the figure only the excess colonies stimulated above the saline control by GM-CSF are shown, with saline addition indicated by closed circles, KI-3G3-14-15 antibody by open circles, and KI-2B7-17-A antibody by closed triangles.

References cited herein are listed on the following pages.

It will be clearly understood that the invention in its general aspects is not limited to the specific details referred to hereinabove.

We claim:

1. A monoclonal antibody, or antibody fragment specific for human granulocyte macrophage-colony stimulating factor (hGM-CSF) receptor, said antibody, or antibody fragment having the ability to inhibit the biological activity of hGM-CSF, and to bind both the high and low affinity hGM-CSF receptor.

2. A monoclonal antibody according to claim 1, said antibody having the ability to inhibit the binding of GM-CSF to the high-affinity hGM-CSF receptor.

3. A monoclonal antibody, or antibody fragment, according to claim 1 that specifically binds the same epitope as an antibody produced by the hybridoma cell line designated KI-2B7-17A as deposited in the European Collection of Animal Cell Cultures (ECACC) under Accession Number 92092317.

4. An antibody fragment according to claim 1.

5. A monoclonal antibody, or antibody fragment according to claim 1, produced by genetic engineering methods.

6. A therapeutic composition comprising a monoclonal antibody according to claim 1 and a pharmaceutically acceptable carrier.

7. A hybridoma cell line producing an antibody according to claim 1.

8. Hybridoma cell line KI-2B7-17-A, as deposited in the European Collection of Animal Cell Cultures (ECACC) under Accession Number 92092317.

9. A method of treatment of a GM-CSF dependent condition, comprising the step of administering to a patient in need of such treatment of an effective amount of an antibody, or antibody fragment according to claim 1, optionally together with a pharmaceutically-acceptable carrier.

10. A method of treatment according to claim 9, wherein the disease to be treated is human myeloid leukemia.

11. A method of mitigation of the side-effects of treatment with GM-CSF, comprising the step of administering to a patient in need of such treatment an effective amount of an antibody, or antibody fragment according to claim 1, optionally together with a pharmaceutically-acceptable carrier.

12. A method of screening of selective antagonists to GM-CSF, comprising the step of utilizing an antibody, or antibody fragment according to claim 1 to identify the specific epitope on the GM-CSF receptor recognized by said antibody and testing putative antagonists of GM-CSF action for the ability to bind to said epitope and inhibit the biological activity of GM-CSF.

13. A therapeutic composition, comprising an antibody fragment according to claim 1 and a pharmaceutically acceptable carrier.

14. A monoclonal antibody according to claim 1, produced by the hybridoma cell line designated KI-2B7-17A, as deposited in the European Collection of Animal Cell Cultures (ECACC) under Accession Number 92092317.

* * * * *